(12) United States Patent
Fogarty et al.

(10) Patent No.: US 6,489,535 B1
(45) Date of Patent: Dec. 3, 2002

(54) NON-MAMMALIAN TRANSGENIC ANIMAL HAVING AN ADULT ONSET NEURODEGENERATIVE PHENOTYPE

(75) Inventors: Patrick Fogarty, Santa Cruz; Joseph Lipsick, Stanford, both of CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

(21) Appl. No.: 09/472,663

(22) Filed: Dec. 27, 1999

Related U.S. Application Data
(60) Provisional application No. 60/148,404, filed on Aug. 11, 1999, and provisional application No. 60/125,586, filed on Mar. 18, 1999.

(51) Int. Cl.$^7$ .......................... G01N 33/00; A01K 67/00; A01K 67/033
(52) U.S. Cl. ...................... 800/3; 800/8; 800/9; 800/12; 800/13
(58) Field of Search ............................... 800/13, 31, 9, 800/221, 12, 3, 8; 435/320.1, 455

(56) References Cited

U.S. PATENT DOCUMENTS

| | | | |
|---|---|---|---|
| 4,670,388 A | 6/1987 | Rubin et al. | 800/25 |
| 5,753,434 A | 5/1998 | Ryner et al. | 435/6 |

FOREIGN PATENT DOCUMENTS

| | | |
|---|---|---|
| WO | WO99/37672 | 7/1999 |
| WO | WO99/55906 | 11/1999 |
| WO | WO 99/64586 | 12/1999 |
| WO | WO99/64859 | 12/1999 |

OTHER PUBLICATIONS

Wall; Transgenic Livestock: Progress and Prospects for the Future, 1996, Theriogenology 45: 57–68.*
Houdebine; Production of pharmaceutical proteins from transgenic animals, 1994, Journal of Biotechnology 34: 269–287.*
Hammer et. al.; Genetic Engineering of Mammalian Embryos, 1986, J. Anim. Sci. 63: 269–278.*
Mullins et. al.; Perspectives Series: Molecular Medicine in Genetically Engineered Animals, 1996, J. Clin. Invest. vol. 98, No. 11: S37–S40.*
Moreadith et. al.; Gene targeting in embryonic stem cells: the new physiology and metabolism, 1997, J. Mol. Med. 75: 208–216.*
Brand, et al, "Targeted Gene Expression as a Means of Altering Cell Fates and Generating Dominant Phenotypes,", Development 118, 1993, pp. 401–415.
Buchanan, et al., "Defective Glia in the Drosophila Brain Degeneration Mutant drop–dead," Neuron, V. 10, May 1993, pp. 839–850.
Feany, et al., "A Drosophila Model of Parkinson's Disease," Nature, V. 404, Mar. 2000, pp. 394–398.
Jackson, et al., "Polyglutamine–Expanded Human Huntingtin Transgenes Induce Degeneration of Drosophila Photoreceptor Neurons," Neuron, V. 21, Sep. 1998, pp. 633–642.
Kretzschmar, et al., "The Swiss Cheese Mutant Causes Glial Hyperwrapping and Brain Degeneration in Drosophila," J. of Neuroscience, V. 17(19), Oct. 1997, pp. 7425–7432.
Marfany, et al., "Identification of a Drosophila Presenilin Homologue: Evidence of Alternatively Spliced Forms," J. Neurogenetics, V. 12(1), pp. 41–54.
Min, et al., "Preventing Neurodeneration in the Drosophila Mutant bubblegum," Science, V. 284, Jun. 1999, pp. 1985–1988.
Min, et al., "Spongecake and Eggroll: Two Hereditary Diseases in Drosophila REsemble Patterns of Human Brain Degeneration," Current Biology, V.7(11), 1997, pp. 885–888.
Price, et al., "Genetic Neurodegenerative Diseases: the Human Illness and Transgenic Models," Science, V. 282, Nov. 1998, pp. 1079–1083.
Rogina, et al., "Drosophila Drop–Dead Mutations Accelerate the Time Course of Age–Related Markers," Proc. Natl. Acad. Sci. USA, V. 94, Jun. 1997, pp. 6303–6306.
Spradling, et al., "Transposition of Cloned P Elements into Drosophila Germ Line Chromosomes," Science, V. 218, Oct. 1982, pp. 341–347.
Warrick, et al., "Expanded Polyglutamine Protein Forms Nuclear Inclusions and Causes Neural Degeneration in Drosophila," Cell, V. 93, Jun. 1998, pp. 939–949.
Gurney, et al. Targeted gene expression as a means of altering cell fates and generating dominant phenotypes. Development. 1993, vol. 118, pp. 401–415, see entire document, especially Fig. 3 (D, E. G).
Ganter, et al., "Myb and Ocogensis".Adv. Cancer Res. 1999, vol. 76, pp. 21–60, see the entire document.
Rottgen, et al. "A genetic screen for elements of the network that regulates neurogenesis in Drosophila". Mol. Gen. 1998, vol. 257, pp. 442–451, see entire document.

\* cited by examiner

*Primary Examiner*—Dave T. Nguyen
*Assistant Examiner*—Quang Nguyen
(74) *Attorney, Agent, or Firm*—Bret E. Field; Bozicevic, Field & Francis

(57) ABSTRACT

Transgenic non-mammalian animals, e.g. flies, that exhibit an adult onset neurodegenerative phenotype, as well as methods for preparing the same, are provided. Also provided are methods of using the subject transgenic non-mammalian animals to identify compounds having activity with respect to adult onset neurodegenerative diseases. Finally, kits for screening compounds for anti-neurodegenerative activity are provided.

10 Claims, No Drawings

NON-MAMMALIAN TRANSGENIC ANIMAL HAVING AN ADULT ONSET NEURODEGENERATIVE PHENOTYPE

CROSS REFERENCE TO RELATED APPLICATIONS

Pursuant to 35 U.S.C. §119 (e), this application claims priority to the filing date of the U.S. Provisional Patent Application Ser. No. 60/148,404 filed Aug. 11, 1999 and U.S. Provisional Patent Application Ser. No. 60/125,586 filed Mar. 18, 1999; the disclosures of which are herein incorporated by reference.

GOVERNMENT RIGHTS

This invention was made with Government support under contract P01 CA70404 awarded by the National Institute of Health. The Government has certian rights in this invention.

INTRODUCTION

1. Field of the Invention

The field of this invention is transgenic flies.

2. Background of the Invention

Adult onset neurodegenerative diseases are among some of the most devastating diseases currently afflicting mankind, at least in the developed nations of the world. Such diseases "are characterized by onset in adult life, chronic progressive course, distinct clinical phenotypes, specific cellular abnormalities involving subsets of neurons, and eventually fatal outcomes." Price et al., Science (Nov. 6, 1998) 282: 1079–1083. Examples of neurodegenerative diseases include: Alzheimer's disease, Parkinson's disease, amyotrophic lateral sclerosis, Huntington's disease, and the like. Currently, treatment of such diseases is limited to disease management and there are no cures. As such, there is much ongoing research that is aimed at the identification and development of new therapeutic agents which can at least slow, if not reverse, the progression of neurodegenerative diseases.

Critical steps in the identification and development of new therapeutic agents are: (a) the generation of candidate agents; and (b) screening of the candidate agents for efficacy (and safety). With the advent of combinatorial chemistry protocols, large numbers of potential compounds, known as libraries, can be rapidly generated. Such libraries serve as a collection of potential therapeutic agents. Following generation of a library of potential therapeutic agents, the library must be screened to identity the promising candidates.

For screening purposes, a number of in vitro high throughput screening protocols have been developed. However, these in vitro screening assays must be followed by in vivo screening assays. Since it is undesirable to immediately screen compounds that show promise from in vitro assays in humans, an important step in the identification of therapeutic agents for such neurodegenerative diseases is the screening of potential therapeutic compounds in non-human animal models. As such, non-human animal models of neurodegenerative diseases play an important role in the discovery of therapeutic agents for such diseases.

One type of non-human animal model that can be used for screening purposes to identify therapeutic agents for use in treating neurodegenerative diseases is a non-human mammalian model, e.g. primates, mice, etc. However, primates are expensive, difficult to use, and require a significant period of time prior to developing adult onset neurodegenerative symptoms. These factors make the use of primates as adult onset neurodegenerative animal models prohibitive. Transgenic mice suffer from analogous disadvantages, i.e. expense, slow reproduction time, and generation of small numbers of offspring.

As such, there is a need for additional animal models of adult onset neurodegenerative diseases. Of particular interest would be the development of an animal model having a relatively short life span and a rapid reproduction cycle characterized by the production of large numbers of offspring. Preferably, such an animal model should also be relatively simple and economic to maintain.

Relevant Literature

Patents of interest include: U.S. Pat. No. 4,670,388. Methods of preparing transgenic *Drosophila melanogaster* are disclosed in: Spradling, A. C., and Rubin, G. M. (1982). Science 218, 341–347; Brand & Perrimon, Development (1993) 118: 401–415; and Phelps & Brand, Methods (April 1998) 14:367–379. See also, Spradling A C, P Element Mediated Transformation in Drosophila: A Practical Approach (ed. D. D. Roberts, IRL Press, Oxford) (1986) pp 175–179. Articles disclosing drosophila that exhibit neurodegenerative phenotypes include: Buchanan and Benzer, Neuron (May 1993) 10: 839–850; Jackson et al, Neuron (September 1998) 21: 633–642; Kretzchmar et al., J. Neuroscience (Oct. 1, 1997) 17: 7425–7432; Marfany et al., J. Neurogenetics (1998) 12: 41–54; Min & Benzer, Current Biology (1997) 7:885–888; Rogina et al., Proc. Nat'l Acad. Sci. USA (June 1997) 94: 6303–6306; and Warrick et al., Cell (Jun. 12, 1998) 93: 939–949.

Articles describing non-human animal models for neurodegenerative diseases include: Price et al., Science (Nov. 6, 1998) 282:1079–1083.

SUMMARY OF THE INVENTION

Transgenic non-mammalian animals, e.g. flies, that exhibit an adult onset neurodegenerative phenotype, as well as methods for preparing the same, are provided. The subject transgenic animals are characterized in that they have a transgene stably integrated into their genome the expression of which in embryonic neuroblasts results in the adult onset neurodegenerative phenotype. In preferred embodiments, the transgene is a myb gene. Also provided are methods of screening compounds for activity with respect to adult onset neurodegeneration, particularly compounds having therapeutic activity with respect to adult onset neurodegenerative disease conditions.

DESCRIPTION OF THE SPECIFIC EMBODIMENTS

Non-mammalian transgenic animals, particularly insects, e.g. flies, that exhibit adult onset neurodegeneration, as well as methods for their preparation, are provided. The subject transgenic animals are further characterized in that they comprise a stably integrated transgene which is expressed in embryonic neuroblasts, where the expressed product results in the observed adult onset neurodegenerative phenotype. In preferred embodiments, the transgene is a myb gene. Also provided are methods of using the subject non-mammalian transgenic animals to screen for compounds having activity with respect to adult onset neurodegeneration, particularly compounds that are therapeutic for neurodegenerative diseases. In further describing the subject invention, the transgenic animals and methods for their production will be detailed first, followed by a discussion of the screening methods of the subject invention.

Animal Models

In the broadest sense, the invention provides non-mammalian animal models that exhibit an adult onset neurodegenerative phenotype, where the phenotype results from a non-adult expression event. In other words, the phenotype of the animal models of the subject invention results from an expression event that occurs in the non-adult animal. The phenotype may result from a variety of different non-adult expression events, where the expression event may be the expression of a mutated gene, the failure of expression of a normally expressed gene, the expression of a transgene, and the like.

In many preferred embodiments, the subject invention provides non-mammalian transgenic animals (i.e. multicellular non-plant organisms) that have an adult onset neurodegenerative phenotype. In other words, the subject transgenic animals exhibit one or more phenotypic traits that characterize neurodegenerative disorders and occur in the adult organism (e.g. during the adult stage of the organism's life), where such traits include: impaired motor skills, impaired cognitive skills, reduced appetite, etc. As such, the subject animals are non-mammalian animal models for neurodegenerative disorders, particularly adult onset neurodegenerative disorders, such as: Parkinson's Disease, Alzheimer's Disease, Huntington's Disease, stroke, and the like. The term transgenic animal is used broadly herein to refer to a non-plant multicellular organism at any stage of development, e.g. adult, fertilized eggs, embryos, larva, etc. Thus, a particular multicellular organism is a transgenic animal according to the subject invention no matter which stage of development it is at, so long as the animal exhibits the requisite adult onset neurodegenerative phenotypic characteristics that results from the correct spatial and temporal expression of the transgene stably integrated into its genome, as described in greater detail infra.

The transgenic animals of the subject invention are non-mammalian transgenic animals. Of particular interest are invertebrate transgenic animals, particularly members of the phylum arthropoda, and more particularly members of the class insecta. Of particular interest in many embodiments are transgenic flies. In many preferred embodiments, the transgenic flies are members of the family Drosophilidae, where the transgenic animal is often a *Drosophila melanogaster*. The subject invention is now further described in terms of transgenic flies.

Transgenic flies of the subject invention, e.g. *Drosophila melanogaster*, exhibit the following phenotypic characteristics: normal wild type phenotype through the initial hours of adult life, where by initial hours is meant at least the first 1 hour, usually at least the first 3 hours and more usually at least the first 5 hours, where in many embodiments the flies may exhibit a normal phenotype through the first 10 to 15 hours of adult life or longer, but in many instances the normal phenotype will cease by about 12 to 13 hours of adult life. Following the initial hours of adult life, the flies exhibit one or more phenotypic characteristic of neurodegeneration, including: progressive loss of neuromuscular control, e.g. of the wings; progressive degeneration of general coordination; progressive degenerative of locomotion; and progressive degeneration of appetite. The subject transgenic flies are further characterized in that death occurs at 4 to 6, usually 4 to 5 days of adult life.

A critical feature of the subject transgenic animals is that the animals harbor a stably integrated transgene that is spatially and temporally expressed in a manner sufficient to result in the desired adult onset neurodegenerative phenotype. The term "transgene" is used herein to describe genetic material which has been or is about to be artificially inserted into the genome of a cell. With regards to spatial expression of the transgene, expression is generally limited to neuronal cells, specifically neuroblasts. With regards to temporal expression, the transgene is required to be expressed in the embryo. In other words, the transgenic expression occurs transiently in the embryonic neuroblasts.

The transgene encodes a product that, when expressed in embryonic neuroblasts, gives rise to the adult onset neurodegenerative phenotype. Generally, the transgene encodes a transcription factor or mimetic thereof having the desired result. Suitable transgenes are those that encode products which activate transcription and can bind to a Myb DNA binding sequence present in the genome of the transgenic animal. Of interest in many embodiments is a myb gene, where the myb gene may be a naturally occurring myb gene or a gene that encodes a product having the desired structural and functional properties, e.g. DNA binding, of the product expressed by a naturally occurring myb gene. Thus, the transgene may comprise a nucleic acid having the sequence of a naturally occurring myb gene or a sequence that includes only a myb domain that governs sequence specific DNA binding (i.e. a myb DNA binding domain) and a transcriptional activation domain. As such, the transgene at least includes a myb DNA binding domain or a sequence that is substantially similar to a naturally occurring myb DNA domain to provide for the requisite DNA binding activity, where substantially similar means a nucleic acid sequence having a sequence identity with a naturally occurring myb DNA binding domain of at least about 50%, usually at least about 60% and more usually at least about 65%, where sequence identity is determined using the BLAST program at default settings. In many embodiments, the transgene comprises a naturally occurring myb gene or a sequence substantially similar thereto. Of particular interest as the transgene is a non-*Drosophila melanogaster* myb gene, preferably a chicken or viral myb gene. Thus, preferred transgenes found in the subject animals are viral or chicken myb genes that encode a product that activates transcription and binds to DNA at a Myb binding sequence. Chicken myb genes of interest include: A-myb and C-myb; while viral myb genes of interest include: v-myb-1151; v-myb-ds7, v-myb-1120 and v-myb-859 (Ganter, B. and J. S. Lipsick (1999) Adv. Cancer Res. (In Press); Ma, X. and B. Calabretta (1994) Cancer Res. 54: 6512–6516; J. S. Lipsick (1996) Oncogene. 13: 223–235; Katzen, A. L., et al., (1998). Genes Dev. 12: 831–843; Garrido, C., et al., (1992) J. Vir. 66: 6773–6776; Fu, S. L. and J. S. Lipsick (1997) Cell Growth Diff. 8: 35–45; Grasser, F. A., et al., (1992) Oncogene 7: 1005–1009; Latham, K. E., et al., (1996) Oncogene 13: 1161–1168; Lane, T., et al., (1990) Mol. Cell. Biol. 10: 2591–2598; Chen, R. H., Fields, S. and J. S. Lipsick (1995) Oncogene 11: 1771–1779; Chen, R. H. and J. S. Lipsick (1993) Mol. Cell. Biol. 13: 4423–4431; Fu, S. L. and J. S. Lipsick (1996) J. Vir. 70: 5600–5610).

As expression of the transgene is targeted to occur in a non-adult stage of the animal, the transgene is stably integrated into the genome of the animal in a manner such that its expression is controlled both spatially and temporally to the desired cell type and the correct developmental stage, i.e. to expression in embryonic neuroblasts. Specifically, the subject transgene is stably integrated into the genome of the animal under the control of a promoter that provides for expression in embryonic neuroblasts. The transgene may be under the control of any convenient promoter that provides for this requisite spatial and temporal expression pattern, where the promoter may be endogenous or exogenous, but will generally be endogenous. A suitable promoter is the promoter located in the *Drosophila melanogaster* genome at position 86E1-3.

The transgene may be integrated into the fly genome in a manner that provides for direct or indirect expression activation by the promoter, i.e. in a manner that provides for either cis or trans activation of gene expression by the promoter. In other words, expression of the transgene may be mediated directly by the promoter, or through one or more transactivating agents. Where the transgene is under direct control of the promoter, i.e. the promoter regulates expression of the transgene in a cis fashion, the transgene is stably integrated into the genome of the fly at a site sufficiently proximal to the promoter and in frame with the promoter such that cis regulation by the promoter occurs.

In yet other embodiments where expression of the transgene is indirectly mediated by the endogenous promoter, the promoter controls expression of the transgene through one or more transactivating agents, usually one transactivating agent, i.e. an agent whose expression is directly controlled by the promoter and which binds to the region of the transgene in a manner sufficient to turn on expression of the transgene. Any convenient transactivator may be employed, where the GAL4 transactivator system is particularly preferred in many embodiments of the subject invention.

In these preferred embodiments of the subject invention in which the transgenic fly comprises the GAL4 targeted expression system, a GAL4 encoding sequence is stably integrated into the genome of the animal in a manner such that it is operatively linked to the endogenous promoter that provides for expression solely in embryonic neuroblasts. Flies of line 31–1 (subsequently referred to as 1822), as disclosed in Brand & Perrimon, Development (1993) 118: 401–415 express GAL4 in this manner, and are known to those of skill in the art. The transgene is stably integrated into a different location of the genome, generally a random location in the genome, where the transgene is operatively linked to an upstream activator sequence, i.e. UAS sequence, to which GAL4 binds and turns on expression of the transgene. Transgenic flies having a UAS: GAL4 transactivation system are known to those of skill in the art and are described in Brand & Perrimon, Development (1993) 118: 401–415; and Phelps & Brand, Methods (April 1998) 14:367–379.

Methods of Producing the Subject Transgenic Flies

The subject transgenic flies can be prepared using any convenient protocol that provides for stable integration of the transgene into the fly genome in a manner sufficient to provide for the requisite spatial and temporal expression of the transgene, i.e. in embryonic neuroblasts. A number of different strategies can be employed to obtain the integration of the transgene with the requisite expression pattern. Generally, methods of producing the subject transgenic flies involve stable integration of the transgene into the fly genome. Stable integration is achieved by first introducing the transgene into a cell or cells of the fly, e.g. a fly embryo. The transgene is generally present on a suitable vector, such as a plasmid. Transgene introduction may be accomplished using any convenient protocol, where suitable protocols include: electroporation, microinjection, vesicle delivery, e.g. liposome delivery vehicles, and the like. Following introduction of the transgene into the cell(s), the transgene is stably integrated into the genome of the cell. Stable integration may be either site specific or random, but is generally random.

Where integration is random, the transgene is typically integrated with the use of transposase. In such embodiments, the transgene is introduced into the cell(s) within a vector that includes the requisite P element, terminal 31 base pair inverted repeats. Where the cell into which the transgene is to be integrated does not comprise an endogenous transposase, a vector encoding a transposase is also introduced into the cell, e.g. a helper plasmid comprising a transposase gene, such as pTURBO (as disclosed in Steller & Pirrotta, "P Transposons Controlled by the Heat Shock Promoter," Mol. Cell. Biol. (1986) 6:1640–1649). Methods of random integration of transgenes into the genome of a target *Drosophila melanogaster* cell(s) are disclosed in U.S. Pat. No. 4,670,388, the disclosure of which is herein incorporated by reference.

In those embodiments in which the transgene is stably integrated in a random fashion into the fly genome, means are also provided for selectively expressing the transgene at the appropriate time during development of the fly. In other words, means are provided for obtaining targeted expression of the transgene. To obtain the desired targeted expression of the randomly integrated transgene, integration of particular promoter upstream of the transgene, as a single unit in the P element vector may be employed. Alternatively, a transactivator that mediates expression of the transgene may be employed. Of particular interest is the GAL4 system described in Brand & Perrimon, supra.

In this particular embodiment, the subject transgenic flies are produced by: (1) generating two separate lines of transgenic flies: (a) a first line that expresses GAL4 in embryonic neuroblasts, e.g. under the control the endogenous fly promoter located at position 86E1-3, described supra; and (b) a second line in which the transgene is stably integrated into the cell genome and is fused to a UAS domain; (2) crossing the two lines; and (3) screening the progeny for the desired phenotype, i.e. adult onset neurodegeneration. Each of the above steps are well known to those of skill in the art. See e.g. Brand & Perrimon, Development (1993) 118: 401–415; and Phelps & Brand, Methods (April 1998) 14:367–379. See also the Experimental Section, infra.

The above strategy is employed to obtain fertilized eggs that comprise the transgene stably integrated into the genome in a manner such that it is expressed in the correct spatial and temporal manner so that the eggs give rise to adult flies exhibiting the desired adult onset neurodegenerative phenotype. Generally, the fertilized eggs are grown at a temperature that results in the adult onset neurodegenerative phenotype, where the temperature ranges from about 24 to 30° C., usually from about 27 to 29° C. and more usually at about 28° C.

Utility

The subject flies find use in a variety.of applications, including: as tools for use in the elucidation of genetic mechanisms involved in neurodegenerative disorders; as a screening tool that identifies therapeutic compounds for use in the treatment of neurodegenerative conditions (i.e. as animal models for human AON disease conditions); and as tools for use in the identification of adult onset neurodegeneration gene targets, i.e. genes whose expression can be modulated, e.g. enhanced or disrupted, in order to alleviate adult onset neurodegeneration. The subject transgenic flies find particular use in screening methods designed to identify therapeutic agents for use in the treatment of neurodegenerative diseases.

Screening Methods

As mentioned above, the subject transgenic flies find particular utility in screening assays designed to identify therapeutic compounds for neurodegenerative conditions, particularly adult onset neurodegenerative conditions. Through use of the subject transgenic flies (or cells derived therefrom depending on the particular screening assay), one can identify compounds that have activity with respect to an adult onset neurodegenerative disease. Compounds have activity with respect to an adult onset neurodegenerative disease if they modulate or have an effect on at least one parameter or symptom of the disease, such as loss of appetite, loss of motor coordination, etc., where the modulatory activity may be to reduce or enhance the magnitude of the symptom. Thus, the screening methods of subject invention can be used to identify compounds that modulate the progression of neurodegenerative disease, e.g. by binding to, modulating, enhancing or repressing the activity of a protein or peptide involved in the progression of the neurodegenerative disease, and/or compounds that ameliorate, alleviate or even remove the phenotypic symptoms of the disease, where such activity may or may not be the result of activity with respect to the underlying mechanism of the disease. Screening to determine drugs that lack effect on the neurodegeneration condition is also of interest. Assays of the invention make it possible to identify compounds which ultimately: (1) have a positive affect with respect to a neurodegenerative disease condition and as such are therapeutics, e.g. agents which arrest or reverse the neurodegeneration or ameliorate or alleviate the symptoms of such a condition; or (2) have an adverse affect with respect to the neurodegeneration disease and as such should be avoided as therapeutic agents.

In the screening methods of the subject invention, a quantity of a candidate agent is generally orally administered to the fly. Following oral administration, the affect of the candidate agent on the adult onset neurodegenerative phenotype of the fly is determined, typically by comparison with a control (i.e. a transgenic fly to which the candidate agent has not been administered). The affect of the candidate agent is determined by determining whether one or more of the phenotypic characteristics of adult onset neurodegeneration are exacerbated or ameliorated in the test fly as compared to the control fly, where characteristics that are monitored include neuromuscular control of wings, general coordination, locomotion, appetite, and the like. The candidate agent is generally orally administered to the fly by mixing the agent into the fly nutrient medium and placing the medium in the presence of the fly, (either the larva or adult fly, usually the adult fly) such that the fly feeds on the medium. Generally a plurality of assay mixtures are run in parallel with different agent concentrations to obtain a differential response to the various concentrations of candidate agent. Typically, one of these concentrations serves as a negative control, i.e. no compound. In a preferred embodiment, a high throughput screening protocol is employed, in which a large number of candidate agents are tested in parallel using a large number of flies. By "large number" is meant a plurality, where plurality means at least 50, usually at least 100, and more usually at least 1000, where the number of may be 10,000 or 50,000 or more, but in many instances will not exceed 5000.

The subject methods find use in the screening of a variety of different potentially therapeutic candidate agents. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modelling.

Screening may be directed to known pharmacologically active compounds and chemical analogs thereof, or to new agents with unknown properties such as those created through rational drug design. Candidate agents having therapeutic activity with respect to adult onset neurodegeneration can be identified based on their ability to at least ameliorate, if not completely alleviate or remove, one or more of the neurodegenerative phenotypes of the adult transgenic fly of the subject invention, such as loss of wing neuromuscular control, and the like, as described above.

The above screening methods may be part of a multi-step screening process of evaluating candidate therapeutic agents for their efficacy (and safety) in the treatment of neurodegenerative diseases in mammalian hosts, e.g. humans. In multi-step screening processes of the subject invention, a candidate compound or library of compounds is subjected to screening in a second in vivo model, e.g. a mouse model, following screening in the subject transgenic animal model. Following the initial screening in the non-mammalian transgenic animals of the subject invention, the positive compounds are then screened in non-human mammalian animal models, including transgenic non-human mammalian animal models. Transgenic mouse models of neurodegenerative diseases and methods for their use in screening assays are described in: U.S. Pat. Nos.: 5,777,194; 5,767,337; 5,720,936; 5,672,805; 5,612,486; 5,602,309; and 5,387,742, the disclosures of which are herein incorporated by reference. In addition, a pre in vivo screening step may be employed, in which the compound is first subjected to an in vitro screening assay for its potential as a therapeutic agent in the treatment of neurodegenerative conditions. Any convenient in vitro screening assay may be employed, where a variety of suitable in vitro screening assays are known to those of skill in the art.

Identification of Gene Targets

In addition to their use as animal models for screening candidate therapeutic agents, the subject transgenic flies also find use in the identification of adult onset neurodegeneration gene targets, i.e. genes whose expression can be beneficially modulated to treat adult onset neurodegeneration. Gene based therapies can be identified by doing traditional enhancer/suppressor analyses in the subject transgenic flies. In these analyses, genes in the subject transgenic flies are mutated to identify ones that either exacerbate or alleviate the adult onset neurodegeneration mutant phenotype. Methods of mutating genes and carrying out enhancer/suppressor analyses are well known to those of skill in the art (Hays, T S et al., Molecular and Cellular Biology (March 1989) 9(3):875–84; Deuring, R; Robertson, B; Prout, M; and Fuller, M T. Mol. Cell. Biol., 1989 9:875–84.; Fuller, M T et al., Cell Mot. Cyto. (1989) 14 :128–35; Rottgen G, Wagner T, Hinz U Mol. Gen. Genet. 1998 257:442–51).

Genes that mutate to enhance the adult onset neurodegeneration phenotype in a recessive manner yield potential protein therapeutics for adult onset neurodegenerative conditions, since elevating the normal gene product level of such genes potentially alleviates the neurodegenerative condition. Genes that mutate to suppress the adult onset neurodegeneration phenotype in a recessive manner yield gene targets for disruption to alleviate the neurodegenerative conditions, where disruption of these genes can be achieved using a variety of methods, ranging from deleting the DNA for the target gene to inhibiting its transcription, translation, or protein activity. For screening candidate agents, small molecule antagonists to these genes can be constructed and evaluated for efficacy in the fly model through oral administration. Alternatively, large molecular antagonists can be delivered by gene therapy, as described infra.

Kits

Also provided by the subject invention are kits for use in performing the subject screening methods. The subject kits include at least a plurality of transgenic flies of the subject invention, or a means for producing such a plurality of flies, e.g. a male and female transgenic fly of the subject invention, vectors carrying requisite genes, such as the transgene, a transposase gene, GAL4, etc. The flies may be housed in appropriate container(s), e.g. vials. The subject kits may also comprise a nutrient medium for the animals, e.g. drosophila medium.

Therapeutic Agents and Pharmaceutical Compositions

Also provided by the subject invention are therapeutic agents for use in treating a neurodegenerative condition, as well as pharmaceutical formulations thereof. The therapeutic agents of the subject invention are those agents identified using the screening methods described supra that show beneficial activity with respect to a neurodegenerative condition, particularly an adult onset neurodegenerative condition (or agents known to have an effect on the expression of a gene identified as modulating the phenotype of an adult onset neurodegenerative condition, where identification employs the use of the subject non-transgenic animals).

Also provided are pharmaceutical compositions of the subject therapeutic agents. In the pharmaceutical compositions or formulations of the subject invention, agents. described above are formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose. derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof (as identified using the mutant screen analysis protocols described supra, it may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Methods of Treating Neurodegenerative Conditions

Also provided are methods of treating neurodegenerative disease conditions, particularly adult onset neurodegenerative disease conditions, using the subject active agents. In the subject methods, an effective amount of the active agent of the subject invention is administered to the host to be treated. By "effective amount" is meant a dosage sufficient to produce a desired result, where the desired result is generally an amelioration or alleviation, if not complete cessation, of one or more symptoms of the neurodegenerative disease being treated. Administration of the agents can be achieved in various ways, including oral, buccal, rectal, parenteral, intraperitoneal, intradermal, transdermal, intracheal,etc. A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Validation of Non-mammalian Animal Models for a Human Disease Condition

Also provided are methods of validating non-mammalian animal models, such as the animal models of the subject invention, as animal models for human disease conditions. In the subject validation methods, a compound having a activity with respect to he human disease of interest is administered to a potential non-mammalian animal model for said disease. The potential animal model may be one that has been identified from nature or produced via human intervention, e.g. genetic engineering. The only limitation on the putative non-mammalian animal model for the human disease of interest is that it have a phenotype that is analogous to the phenotype suffering from the human disease, i.e. it has a phenotype that can be correlated to at least one symptom of the disease in a human. For example, the animal models of the present application have a phenotype that is analogous to the phenotype of a human suffering from an adult onset neurodegenerative disease condition.

Following administration of the compound to the putative non-mammalian animal model, the effect that the compound has on the phenotype of the non-mammalian animal phenotype observed. Based on the observation, a determination is made as to whether the compound has the same effect on the phenotype of the non-mammalian animal model as it does on the human disease phenotype. For example, where the compound improves the impaired appetite in a human suffering from the human disease and also improves the impaired appetite of the putative non-mammalian animal model, the compound has the same effect on the phenotype of the animal model as it does on the phenotype of a human suffering from the disease.

If the compound has the same effect on the phenotype of the putative non-mammalian animal model as it does on a human suffering from the disease, the non-mammalian animal model is validated as an animal model for the human disease condition.

The following examples are offered by way of illustration and not by way of limitation.

EXPERIMENTAL

I. Methods and Materials

A. Vectors and Genes Used myb genes were cloned into the polylinker of the pUAST such that the UAS vector sequences were adjacent to the 5' end of the myb genes (Brand et al. 1993,supra). Transcription of these constructs was controlled by GAL4, which needs to bind to the UAS sequence to drive expression of the gene that has been cloned into the pUAST vector. The pUAST-myb constructs were integrated into the genome of Drosophila melanogaster by standard microinjection procedures (Spradling, A. C., and Rubin, G. M. (1982). Science 218, 341–347).The transposase source used to stimulate the integration of the pUAST-myb constructs into the genome was provided by co-injecting the vector pTURBO (as described in Steller & Pirrotta, (1986) supra). The following myb genes were cloned into the pUAST vector: Drosophila myb, chicken A-myb, chicken B-myb, chicken c-myb, AMV v-myb-1151, AMV v-myb-1120, AMV v-myb-1151 -ds7, AMV v-myb-1151-C65S, and AMV v-myb-1151-859. (Ganter, B. and J. S. Lipsick (1999) Adv. Cancer Res. (In Press); Ma, X. and B. Calabretta (1994) Cancer Res. 54: 6512–6516; J. S. Lipsick (1996) Oncogene. 13: 223–235; Katzen, A. L., et al., (1998). Genes Dev. 12: 831–843; Garrido, C., et al., (1992) J. Vir. 66: 6773–6776; Fu, S. L. and J. S. Lipsick (1997) Cell Growth Diff. 8: 35–45; Grasser, F. A., et al., (1992) Oncogene 7: 1005–1009; Latham, K. E., et al., (1996) Oncogene 13: 1161–1168; Lane, T., et al., (1990) Mol. Cell. Biol. 10: 2591–2598; Chen, R. H., Fields, S. and J. S. Lipsick (1995) Oncogene 11: 1771–1779; Chen, R. H. and J. S. Lipsick (1993) Mol. Cell. Biol. 13: 4423–4431; Fu, S. L. and J. S. Lipsick (1996) J. Vir. 70: 5600–5610). pGAWB (Brand et al. 1993) was used to identify endogenous regulatory sequences and use them to control expression of transgenic genes.

B. Gene Expression

The vector pGAWB was inserted (via transposase) at different places in the genome. This vector contains a GAL4 gene that has a very weak promoter, which enabled the identification of the regulatory region that controls gene expression. Some of these integrations are such that endogenous regulatory elements control the expression of the GAL4 gene. Many enhancer lines of flies have been identified that produce discrete GAL4 expression patterns (Brand et al. 1993, supra). Specifically, GAL4 expressing stocks #1822 and 2689 from the Bloomington stock center in Indiana (URL having an address made up of the word "flybase.bio.indiana" flanked by "www." and ".edu") have neural expression patterns in either the neuroblasts (neuron progenitors) or neurons, respectively (Brand et al. 1993, supra, Lopez 1995 (URL having an address made up of the word "flybase.bio.indiana" flanked by "www." and ".edu").

C. Molecular Identification of the Neuroblast Expressing Promoter

Plasmid rescue was preformed on stock 1822. Briefly, genomic DNA was isolated using standard techniques, treated with restriction endonuclease (either XhoI, SacII, or SalI), heat to inactivate the restriction enzyme, treated with DNA ligase, and used to transform *E. coli,* followed by plating of the bacteria on nutrient plates containing Ampicillin. The only bacteria that were capable of growing contained the ampicillin resistance gene from the P element. The important elements that were cloned from the genomic DNA are the ampicillin resistance gene and a bacterial origin of replication from the P element sequences plus genomic DNA that is immediately adjacent to the P element insertion. A SacII/SalI fragment was used as a probe for in situ hybridization to the polytene chromosomes, which is the standard technique for physically mapping DNA to a position in the Drosophila genome. Additionally, this fragment was also used as a probe on Southern blots to identify P1 clones that contain this region of DNA sequences. Clone #2617 was one such P1 construct identified from the Flybase library of ordered genomic P1 clones as containing the regulatory DNA for embryonic neuroblast expression (URL having an address made up of the word "flybase" flanked by "www." and ".org").

D. Screening Compounds in the Fly

Each compound was prepared over a range of dilutions and each was tested for the activity of alleviating the adult onset neurodegeneration condition. The compound dilutions were uptaken by either the larva or adult flies. The compound dilutions were mixed into the nutrient media and this served as the food/water source for either larva or flies. The adult onset neurodegeneration symptoms and their timelines were monitored for each compound dilution and compared to the no treatment control. Compounds examined here included: beta-estradiol, zinc chloride, sodium chloride, water, chocolate, and phosphate buffered saline.

II. Results

A. myb Genes and Adult Onset Neurodegeneration

Flies containing the pUAST-v-myb-1151 construct were mated to the 1822 GAL4 producing fly strain (as described in Brand (1993) supra) and their progeny were allowed to develop at a variety of temperatures spanning the range that Drosophila are raised at, i.e. 18, 20, 23, 25, and 28° C. At all temperatures the progeny developed normally into adult flies, however at the temperatures >23° C. the adult lifespan was dramatically reduced. The adults showed a characteristic and progressive degenerative phenotype during their adult life. Specifically the flies would lose control of their wings between 1 and 3 hours of adult age, followed by wing paralysis between 3 and 24 hours, then loss of coordination and locomotion capabilities between 24 and 36 hours. The flies then stopped eating/drinking which lead to death between 72 and 144 hours of adult age. Raising the embryos at the higher temperature (>23° C.) and then transferring the larva to lower temperatures is sufficient to induce the adult onset phenotypes. The reciprocal is also true, raising the embryos at low temperature (18–20° C.) and then transferring the larva to high temperature (28° C.) fails to induce the adult onset phenotypes. These findings are consistent with the known expression pattern of line 1822, which is in the embryonic neuroblasts (Brand et al. 1993).

General neural expression of any myb gene does not result in the adult onset neurodegenerative phenotype. The fly strain 2689 expresses GAL4 in all neurons. Using this fly strain to drive the expression of myb genes has no effect on the resulting progeny at any temperature. This further suggests that myb expression in the neuroblast, the neuron progenitor, is sufficient to induce the adult onset neurodegeneration phenotype.

As the myb family of genes has many members with different biochemical properties and physiological functions, other myb genes that represent various biochemical and physiological divergence were tested for generating the adult onset neurodegenerative phenotype. The results suggested that the neurodegenerative phenotype correlates with myb genes that can bind to DNA and activate transcription.

B. Embryonic Neuroblast Regulatory Region

The P element (which contains the promoterless GAL4 gene) in fly strain 1822 has landed in proximity to a regulatory element that gives an embryonic neuroblast expression pattern. As regulatory elements in Drosophila melanogaster are typically simple, the genomic DNA sequences flanking the P element insert were cloned by standard plasmid rescue techniques. The promoter region was localized to chromosome position 86E1-3. Further, P1 clones that contain the promoter region were identified and mapped with restriction endonucleases. Line 1822 may represent a subset of the prospero regulatory region based on the following:

Both localized to the 86E 1-3 area in the genome;

Both drive expression in the embryonic neuroblast cells; and

The full length prospero regulatory region in trans to vmyb yield a similar, but stronger effect on the developing fly than does line 1822 in trans to vmyb.

C. Screening compounds in Drosophila

To test whether this AON mutant condition is a good model for human AON conditions (Alzheimer's, stroke, Parkinson's, etc.), compounds known to influence human AON conditions were administered orally to the mutant AON fly strain. In addition, compounds were also tested in the AON mutant fly strain that were known not to influence human AON conditions. Finally, a complex mixture with unknown influence on human AON conditions was tested in the AON mutant fly strain.

Estrogen was tested and yielded the following observed results:

TABLE 5

Estrogen appears to delay the progression of the AON phenotype. Estrogen has similar roles as a putative neuroprotecting molecule in Alzheimer's, Parkinson's, and stroke as well as in the AON fly.

| Age of Adult | Phenotypes for wild-type and AON flies fed estrogen | | | |
| --- | --- | --- | --- | --- |
| (hours) | Wt | AON | Wt + E | AON + E |
| 0–1 | None | None | None | None |
| 1–3 | None | WC | None | None |
| 3–24 | None | WP | None | WC |
| 24–36 | None | C | None | WP |
| 36–72 | None | L | None | C |
| 72–144 | None | D | None | L |
| 144+ | None | — | None | D |

None = normal adult fly
WC = loss of wing control
WP = wings paralyzed
C = loss of coordination and locomotion capabilities
L = flies stop uptaking liquid
D = death
Wt = wild-type adult flies
Aon = Aon mutant adult flies
E = larva fed .5 µg/ml estrogen Each experiment represents 100 flies examined in two independent tests. >90% of the flies exhibited each phenotype ascribed to them.

Orally administered estrogen appears to have therapeutic benefit for alleviating the neurodegenerative damage caused by both stroke and Alzheimer's in humans. Similarly, estrogen also alleviates the AON condition in the mutant fly strain when administered orally.

Zinc and Aluminum have been reported to exacerbate Alzheimer's disease in humans. Zinc was orally administered to the AON mutant fly strain. At low concentrations (10–20 µgrams/ml of nutrient media), no effect was observed on the mutant AON fly strain. However, at higher concentrations (50–100 μgrams/ml of nutrient media) the zinc exacerbated the AON condition.

Two compounds (sodium chloride and phosphate buffered saline) that do not have any known effect on human AON conditions, also showed no effect on the AON phenotype in the mutant fly strain. Finally, a saturated solution of chocolate in water was made and was fed to the mutant fly strain over a dose range of 1–100 μl/ml of nutrient media. No effects were observed on the AON phenotype over this dose range. Chocolate's impact on any human AON conditions has not been assessed.

III. Additional Drug Screening

To validate the AON fly for drug discovery relevant to human biology and diseases, this fly strain was subjected to an extensive array of chemicals that are known to have their effect on the human nervous system.

| Chemical tested | Drug name | Dose (mg/ml) | result |
|---|---|---|---|
| Alzheimer's Disease | | | |
| Tacrine | Cognex | .0005 | S increased 100% |
| Propentofylline | Pending | 5 | L.D. 80, escapers - S increased 200%, D increased 17% |
| Alpha Tocopherol | Vitamin E | 1 | L.D. 30, escapers - S increased 200%, D increased 33% |
| Nicotinamide | Nicotine | 5 | L.D. 90, S increased 100% |
| Parkinson's | | | |
| Lisuride | Revanil | 2 | L.D. 100 |
| | | .2 | L.D. 100 |
| | | .02 | L.D. 99 (no AON flies) |
| | | .002 | L.D. 60, S increased 100% |
| Selegiline | Carbex | 2 | L.D. 100 |
| | | .2 | AON class only, L.D. 95, escapers - No Effect |
| | | .02 | S increased 100% |
| | | .0002 | S increased 200% |
| Benztropine | Cogentin | .23 | L.D. 100 |
| | | .023 | AON class L.D. 95, escapers delayed >5 days; S increased 500% |
| | | .00023 | S increased 300%, D increased 17% |
| | | .000023 | S increased 400%, D increased 33% |
| Bromocriptine | Parlodel | .1 | L.D. 100 |
| | | .01 | S increased 33% |
| | | 001 | S increased 33% |
| Trihexyphenidyl | Artane | 1 | L.D. 95 for AON class, escapers - S increased 33% |
| | | .1 | S increased ~25% |
| Levodopa | Dopar | .00015 | S increased 100% |
| Other AON diseases | | | |
| Stroke | Dizocilipine | Pending | .6 | L.D. 100 |
| | | .06 | AON growth delayed, No Effect |
| | | .0006 | AON symptoms delayed 2 days |
| | | .00006 | S increased 17% |
| Alzheimer's, Parkinson's, stroke | Estrogen | ERH therapy | 5 | S increased 100%, D increased 68% |
| | | .5 | S increased 200% |
| Amyloid Lateral Sclerosis | Riluzole | Rilutek | 1 | L.D. 100 |
| | | .1 | L.D. 100 (some pupa) |
| | | .01 | S increased 100%, D increased 17% |
| Misc. neurochemicals | Neural Depressive | Diazepam | .1 | L.D. 100 |
| | | .01 | No Effect |
| | | .001 | No Effect |
| | | .0001 | No Effect |
| | | .00001 | No Effect |
| | Neural degenerator | Nitric oxide | .1 | AON specific L.D. 100 |
| | | .1 | AON specific L.D. 75 |
| | Neurohormone | Melatonin | 5 | L.D. 100 |
| | | .5 | No Effect |
| | | .05 | No Effect |
| | | .005 | No Effect |
| | | .0005 | No Effect |
| | Neurohormone | Chocolate | 5 | No Effect |
| | | .5 | No Effect |
| | | .05 | No Effect |
| | | .005 | No Effect |
| | | .0005 | No Effect |

S = AON symptom free adult time span
D = life span

Summary of the effects that neuromodulating effect in humans, in the AON fly.

Four (of six tested) drugs known to influence Alzheimer's disease (propentofylline, estrogen, alpha tocopherol, and nicotinamide), Seven (of eight tested) drugs known to influence Parkinson's disease (levodopa, bromocriptine, estrogen, selegiline, trihexyphenidyl, lisuride, benztropin), Two (of two tested) drugs known to influence stroke (dizocilipine, estrogen), One (of one tested) drug known to treat ALS (riluzole).

It is interesting to note that bromocriptine, lisuride, and pergolide are all dopamine agonists for the treatment of Parkinson's, but pergolide did not show any effect while the other two did. This mirrors the human situation—pergolide shows less efficacy than bromocriptine or lisuride in Parkinson's patients. Finally, this drug screening method appears to be targeted at identifying anti-neurodegenerative compounds with a high degree of specificity as only ~0.0025% of random chemicals tested in this manner are identified as a positive against AON.

Unknown compounds were screened in the AON fly for their ability to prevent neurodegeneration. The high throughput screen has yielded the following information: 3,200 assays were preformed and analyzed by 1 person in 14 days. From this screening process, 20 distinct compounds scored as positives and are being further examined.

It is evident from the above results and discussion that the subject invention provides a valuable screening tool for use in the evaluation of potential therapeutic agents for use in the treatment of adult onset neurodegenerative disorders. Advantages of using the subject transgenic flies for screening potential therapeutic candidates include: adaptability of the subject flies to high throughput screening protocols, simplicity and low cost of maintaining the subject flies, ability of the subject flies to identify potentially orally active therapeutic agents, rapid reproduction of the subject flies, and ability of the subject flies to produce large numbers of offspring. As such, the subject invention fills a void in the existing arsenal of screening tools, in that the subject invention provides a means for conducting in vivo high throughput screening assays. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A transgenic *Drosophila melanogaster* that exhibits an adult onset neurodegenerative phenotype, wherein said transgenic *Drosophila melanogaster* comprises a myb transgene in its genome that is expressed in embryonic neuroblasts.

2. The transgenic *Drosophila melanogaster* according to claim 1, wherein said myb transgene encodes a product that binds to DNA and activates transcription.

3. The transgenic *Drosophila melanogaster* according to claim 1, wherein said myb transgene is a chicken or viral myb gene.

4. A kit for use in screening compounds for alleviating the adult onset neurodegenerative condition, said kit comprising:

transgenic *Drosophila melanogaster* according to claim 1 and a suitable container.

5. The kit according to claim 4, wherein said kit further comprises nutrient medium for said transgenic *Drosophila melanogaster*.

6. A method of screening a candidate compound for alleviating the adult onset neurodegenerative condition, said method comprising:

administering said compound to the transgenic *Drosophila melanogaster* according to claim 1;

comparing the adult onset neurodegenerative condition in said transgenic *Drosophila melanogaster* with the adult onset neurodegenerative condition in a control transgenic *Drosophila melanogaster* that did not receive said candidate compound, wherein a decrease in the adult onset neurodegenerative condition of the treated transgenic *Drosophila melanogaster* is indicative of the alleviating activity of the candidate compound.

7. The method according to claim 6, wherein said compound is orally administered to said transgenic *Drosophila melanogaster*.

8. A method of screening a candidate compound for alleviating the adult onset neurodegenerative condition, said method comprising:

feeding said compound to the transgenic *Drosophila melanogaster* according to claim 1;

comparing the adult onset neurodegenerative condition in said transgenic *Drosophila melanogaster* with the adult onset neurodegenerative condition in a control transgenic *Drosophila melanogaster* that did not receive said candidate compound, wherein a decrease in the adult onset neurodegenerative condition of the fed transgenic *Drosophila melanogaster* is indicative of the alleviating activity of the candidate compound.

9. The method according to claim 8, wherein said candidate compound is present in a nutrient medium.

10. A method of screening a plurality of candidate compounds for alleviating the adult onset neurodegenerative condition, said method comprising:

feeding said plurality of compounds to a plurality of the transgenic *Drosophila melanogasters* according to claim 1 in a manner sufficient to ensure that each of said transgenic *Drosophila melanogasters* is fed only a single type compound from said plurality of candidate compounds;

comparing the adult onset neurodegenerative condition in said plurality of transgenic *Drosophila melanogasters* with the adult onset neurodegenerative condition in control transgenic *Drosophila melanogasters* that did not receive said plurality of candidate compounds, wherein a decrease in the adult onset neurodegenerative condition of the fed transgenic *Drosophila melanogasters* is indicative of the alleviating activity of said plurality of candidate compounds.

* * * * *